United States Patent
Fischer et al.

[11] Patent Number: 6,113,590
[45] Date of Patent: Sep. 5, 2000

[54] HEART CATHETER WITH MEANS FOR MEASURING THE CONTACT

[75] Inventors: Harald Fischer; Martin Vallendor, both of Karlsruhe; Klaus-Peter Brhel, Philippsburg, all of Germany

[73] Assignee: Forschungszentrum Karlsruhe GmbH, Karlsruhe, Germany

[21] Appl. No.: 09/195,088

[22] Filed: Nov. 18, 1998

[30] Foreign Application Priority Data

Nov. 22, 1997 [DE] Germany .................. 197 51 875

[51] Int. Cl.⁷ ............................................. A61B 18/04
[52] U.S. Cl. .......................... 606/28; 606/27; 606/28; 73/800; 600/486
[58] Field of Search ..................... 606/2, 28, 13–18, 606/27, 33–50, 149, 185; 128/634, 642, 657, 662.05, 667, 670, 673, 674, 898; 607/88–94; 600/300, 374, 485, 486, 561; 73/720, 800; 604/53, 96, 280; 250/339.12

[56] References Cited

U.S. PATENT DOCUMENTS

| | | | |
|---|---|---|---|
| 4,503,023 | 3/1985 | Breck et al. | 423/328 |
| 4,711,770 | 12/1987 | Skeeis et al. | 423/328 |
| 4,757,041 | 7/1988 | Oleck et al. | 502/65 |
| 4,837,396 | 6/1989 | Herbst et al. | 502/67 |
| 5,279,726 | 1/1994 | Ward | 208/111 |
| 5,350,501 | 9/1994 | Ward | 208/111 |
| 5,413,977 | 5/1995 | Occelli | 502/68 |

FOREIGN PATENT DOCUMENTS

| | | | |
|---|---|---|---|
| 0140608 | 8/1985 | European Pat. Off. | B01J 29/28 |
| 0247678 | 2/1987 | European Pat. Off. | C10G 47/20 |
| 0247679 | 2/1987 | European Pat. Off. | B01J 29/08 |
| 0559646 | 10/1994 | European Pat. Off. | B01J 29/06 |
| WO 91/17829 | 11/1991 | WIPO | C10G 47/20 |
| WO 93/02159 | 2/1993 | WIPO | C10G 47/02 |
| WO 94/26847 | 11/1994 | WIPO | C10G 47/16 |
| WO 95/02653 | 1/1995 | WIPO | C10G 11/05 |
| WO 97/20016 | 6/1997 | WIPO | C10G 47/16 |

*Primary Examiner*—Linda C. M. Dvorak
*Assistant Examiner*—A. Farah
*Attorney, Agent, or Firm*—Klaus J. Bach

[57] ABSTRACT

In a probe disposed at the distal end of a heart catheter for the coagulation of muscle and connective tissues by subjecting them to a high frequency field, a pressure sensor is provided for measuring the axial force effective on the probe tip which pressure sensor inlcudes a plastic body with an axial bore into which a light conductor extends and which has at its end opposite the light conductor a mirror for reflecting light supplied through the light conductor back into the light conductor. The plastic body is resiliently movably supported with respect to the light conductor so that the light reflected by the mirror back into the light conductor depends on the displacement of the probe tip caused by a pressure force applied to the probe tip.

6 Claims, 1 Drawing Sheet

HEART CATHETER WITH MEANS FOR MEASURING THE CONTACT

BACKGROUND OF THE INVENTION

The invention relates to a heart catheter with a probe disposed at the distal end of the catheter for the high frequency coagulation of tissue and a temperature sensor for measuring the heating of the coagulation area during the procedure. The high-frequency technical equipment corresponds to those used in known coagulation arrangements. The invention resides in the probe at the distal end of the catheter. The temperature sensor is in contact with the inside surface of the electrically conductive tip of the probe. Supply and return lines as well as the high frequency line extend in the interior of the catheter.

It is important that the release of HF energy to the surrounding muscle and connective tissue is well controlled. Measuring the temperature provides for an indirect and time-delayed indication of the quality of the procedure. Obtaining immediate information concerning the coagulation process, essentially on a real-time basis, would be helpfull for safely performing the procedure. It is noted that there is a danger that the tissue is damaged in the coagulation area or even that the tissue is penetrated by the catheter.

It is the object of the present invention to provide a heart catheter by which the coagulation procedures can be performed on the heart by well known techniques but wherein, at the same time, the engagement pressure of the probe tip in contact with the muscle or connective tissue can be determined so that injuries can be greatly limited.

SUMMARY OF THE INVENTION

In a probe disposed at the distal end of a heart catheter for the coagulation of muscle and connective tissues by subjecting them to a high frequency field a pressure sensor is provided for measuring the axial force effective on the probe tip which pressure sensor inlcudes a plastic body with an axial bore into which a light conductor extends. At its end opposite the light conductor the probe has a mirror for reflecting light supplied through the light conductor back into the light conductor. The plastic body is resiliently movably supported with respect to the light conductor so that the amount of light reflected by the mirror back into the light conductor depends on the displacement of the probe tip caused by a pressure force applied to the probe tip.

With the probe which becomes wider toward the pressure sensor the axial contact pressure is measured optically: Light is transmitted by way of the light conductor, through a cylindrical open space and directed onto the mirror and is reflected solely by the mirror. The reflected light beam which is again coupled into the light conductor returns to the catheter handling area and to an optical coupling arrangement. In this arrangement, an optical measuring and reference signal are formed and supplied to an electronic signal processing unit wherein the length of the hollow space between the light conductor front face and the mirror which depends on the axial force effective on the probe, or the sensor respectively, is determined. It is important however, that the reflection properties of the mirror do not change when there is a temperature difference between the mirror and the surrounding area. In order to maintain a stable reflection propertiy, the mirror has an appropriate reflection surface.

The resiliency of the probe, or respectively, the sensor is obtained in one embodiment in that the hollow space between the light conductor front face and the mirror consists of a rubber-like elastic substance such as silicon rubber and, in another embodiment, merely of a bore in the plastic carrier, the plastic carrier being coupled with the catheter end by a coil spring.

In the first embodiment, the silicon rubber may be a silicon hose disposed in the plastic carrier which silicon hose is compressed under pressure. The rubber hose can be compressed up to the point where the opening inside the hose disappears fully under the effects of the axial compression forces on the tip of the probe—and even further. As a result, the radiation energy measured decreases with increasing pressure on the probe tip. For safe guidance of the probe, the proximal end section thereof is diposed in a guide tube which is firmly attached to the catheter end.

If the plastic carrier has, at its proximal end, a coaxial hollow cylindrical extension of smaller diameter over which the end area of a coil spring is disposed and by which the coil spring is guided and abuts the distal end face of the catheter, the space between the mirror and the light conductor front face becomes shorter when an axial pressure or force is applied to the probe tip, without causing any change in the opening cross-section. This results in an increase of the light energy returned through the light conductors. The arrangement may be disposed within an outer tube for safety reasons.

For a constantly uniform reflection capability, the mirror is preferably provided with a highly polished reflection surface of platinum. Although this is expensive, the platinum treatment provided for good reflection qualities which could be maintained during use which result was not reliably obtained with other protective coatings.

The heart catheter combines three functions: it forms a device for coagulation, it permits the measurement of the heating of the tissue in the coagulation area in the well known manner and it permits the probe to sense the axial force on the probe tip. In this way, tissue damage can be controlled and the dreaded worst case of penetration of the heart wall, which would require emergency opening of the chest and other problematic emergency procedures, can be avoided. A heart catheter which includes such pressure sensing equipment facilitates therefore a sensitive and careful treatment.

DESCRIPTION OF PREFERRED EMBODIMENTS

Figure 1:
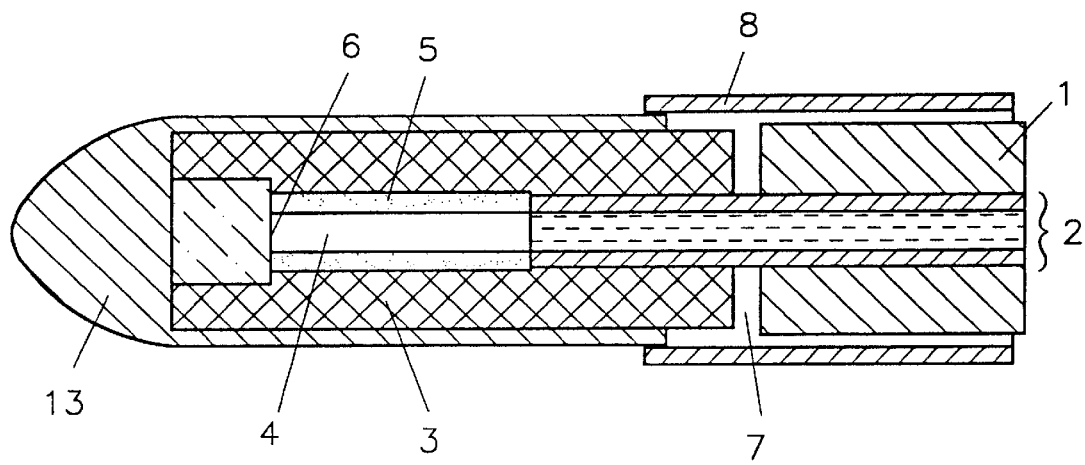
FIG. 1 shows an HF coagulation probe having integrated therein a pressure sensor using the elasticity of a material.

FIG. 1 shows in principle the probe sensor in an axial cross-sectional view. The light conductor 2 projects axially from the heart catheter end and extends into an axial bore forming the empty space 4 in the plastic carrier 3 which consists of silicon rubber. In the open space 4, the light conductor 2 is in direct contact with the compressible rubber tube 5, which has an open cross-section corresponding to that of the actual light conductor. The other end of the rubber tube 5 engages the mirror 6, which is provided with a flat platinum coated and highly polished reflection surface.

Between the catheter end 1 and the plastic carrier 3, there is a gap 7 which permits axial movement of the probe. The gap 7 is sufficiently wide that the rubber tube 5 can be compressed up to the point where its open cross-section disappears. From this limit position on, no light can be transmitted from the light conductor 2 through the rubber tube 5 to the mirror 6 to be reflected and returned. The reflection at the rubber tube wall is minimal since the rubber tube wall is non-reflective. It is possible to apply a greater pressure to the probe tip, but this is out of the measuring range that is further reduction of the light intensity is not possible.

In order to provide for a stable and reliable guidance for the probe, a guide tube 8 extends around the end area of the heart catheter and the adjacent part of the probe such that only axial movement of the probe relative to the catheter 1 is permitted. The spring-elastic element, which holds the probe away from the catheter 1, is the rubber tube 5 which provides for the highest light flux when there is no axial force on the probe tip.

Figure 2:
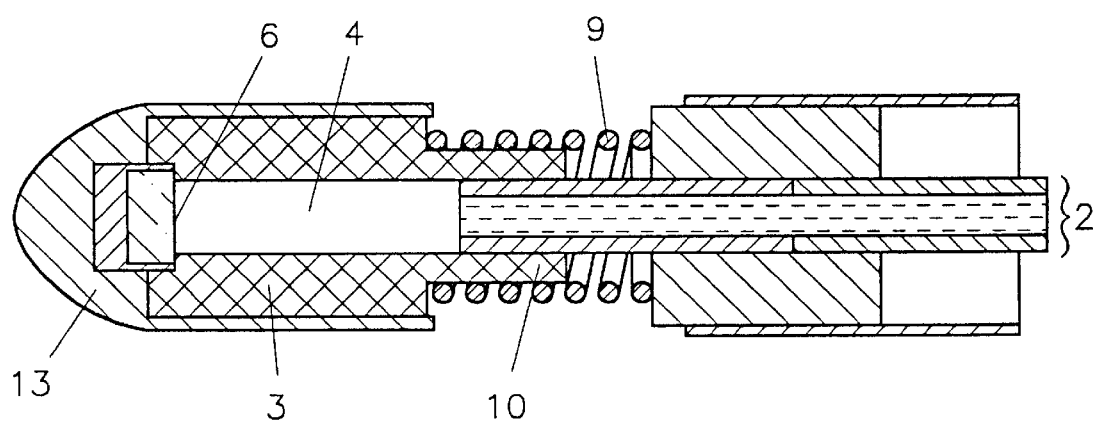
FIG. 2 shows an HF coagulation probe with integrated spring-elastic sensor.

FIG. 2 uses as spring element a coil spring instead of the rubber tube as shown in FIG. 1. In this case, the plastic carrier consisting of PEEK (Poly Ether Ether Ketane) or POM (Poly Oxy Methylene) is provided, at its proximal end, with a cylinder structure 10 of reduced cross-section but of the same plastic material, over which the coil spring 9 is disposed. With its opposite end, it abuts the front end of the heart catheter. The light conductor extends into the bore 4 like in the example of FIG. 1. The open space between the light conductor end and the mirror 6 which is also provided with a highly polished platinum coated reflection surface always has the full width of the outer diameter of the light conductor end. However, its axial length is the greatest in a force-free state, that is the travel distance of the light from light conductor end to the mirror and back to the light conductor is the greatest. In this position, the reflected light arriving at the proximal end of the light conductor exhibits the lowest light intensity.

When an axial force is effective on the probe tip in the direction toward the heart catheter the distance between the mirror 6 and the light conductor end becomes smaller whereby more light is reflected and returned into the light conductor.

The probe tip is guided essentially by the light conductor sleeve, but it can additionally be guided by a guide tube like in the arrangement of FIG. 1.

Figure 3:
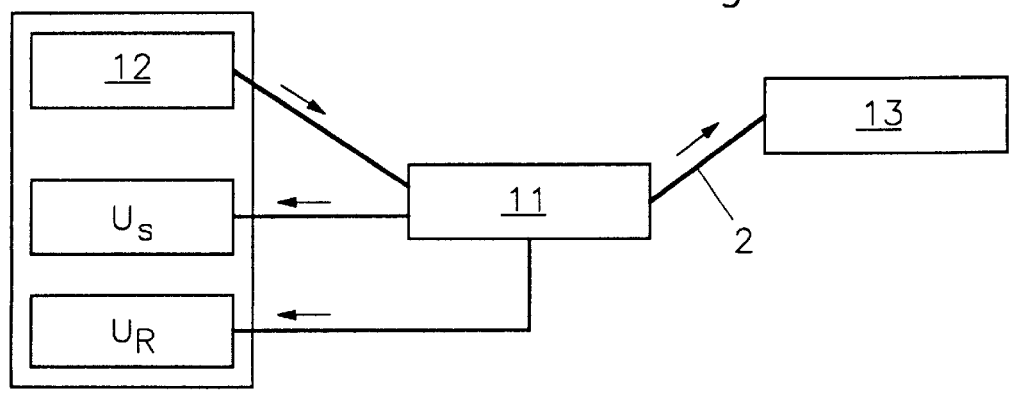
FIG. 3 is a block diagram for the opto-electronic evaluation.

In the arrangement of FIG. 1, the light output becomes smaller as pressure is applied to the probe tip; in the arrangement of FIG. 2, the light output is increased under the same circumstances. A commercially available opto-coupler as it is schematically shown in FIG. 3 generates the optical measuring and reference signals. For the evaluation and processing of the optical signals, an also commercially available electronic evaluation unit is utilized which is connected to the opto coupler. The calibration requirements of the opto-electronic equipment are essentially the same for the arrangement with decreasing light output (FIG. 1) as for the arrangement with increasing light output (FIG. 2).

The light conductor 2 extending from the coupler 11 to the heart catheter end is a flexible glass rod or a fiber bundle.

Both arrangements are provided with an opaque, somewhat stiff, sleeve. The measurement signal ($U_S$) consists of light energy supplied to the probe and light energy returning therefrom wherein only the returning light energy is variable. The measuring signal is compared with the reference signal ($U_R$) which represents the supply light energy which is always constant.

All the materials of the probe with the integrated sensor are suitable for medical applications, that is, they are compatible with the tissue and are able to withstand the necessary cleaning and sterilization procedures. Because of the safety requirements for medical applications, the catheter is disposed within a hermetically sealed sleeve up to the contact area necessary for the coagulation procedure.

What is claimed is:

1. A probe disposed at a distal end of a heart catheter for the coagulation of muscle and connective tissues, said probe including a pressure sensor for measuring an axial force effective on the tip of said probe, said probe comprising: a hard, tissue-compatible plastic carrier having an axial bore, a light conductor projecting from said distal catheter end and extending into said bore, a mirror with a reflection surface having reflection properties which do not change with temperature differences with respect to the surrounding area arranged in said bore and having a mirror surface disposed in a plane normal to the axis of said bore and directed toward said light conductor such that a light beam exiting the light conductor and reaching said mirror surface is reflected back into said light conductor, said bore forming between said light conductor and said mirror an open axial space having a non-reflective wall and said probe tip being axially movably disposed relative to said light conductor such that said open axial space is shortened when a pressure is effective on said probe tip and a resilient rubber tube fitted into said bore between said mirror and said light conductor, said rubber tube having an open inner cross-section corresponding to the light conductive cross-section of said light conductor, said rubber tube being axially compressed when said probe tip is subjected to an axial compression force whereby the open inner cross-section of the rubber tube is reduced and the amount of light permitted to pass therethrough and returned into said light conductor is thereby restricted, so that the light energy reflected back into said light conductor depends on the axial pressure force effective on said probe tip.

2. A probe according to claim 1, wherein said rubber elastic tube consists of silicon rubber.

3. A probe according to claim 2, wherein a guide tube extends from said catheter so as to receive and axially guide said probe.

4. A probe according to claim 1, wherein a guide tube extends from said catheter end so as to receive, and axially guide, said probe.

5. A probe according to claim 1, wherein said mirror has a light reflection surface consisting of a highly polished platinum layer.

6. A probe according to claim 5, wherein said plastic carrier consists of one of PEEK and POM.

* * * * *